United States Patent [19]

Voss et al.

[11] Patent Number: 4,548,825

[45] Date of Patent: Oct. 22, 1985

[54] METHOD FOR INK-JET PRINTING ON UNCOATED TABLETS OR UNCOATED TABLET CORES

[75] Inventors: Günther Voss, Diessen; Peter Gruber, Biberach, both of Fed. Rep. of Germany

[73] Assignee: Boehringer Ingelheim GmbH, Ingelheim am Rhein, Fed. Rep. of Germany

[21] Appl. No.: 538,200

[22] Filed: Oct. 3, 1983

Related U.S. Application Data

[63] Continuation of Ser. No. 284,985, Jul. 20, 1981, abandoned, which is a continuation-in-part of Ser. No. 147,841, May 8, 1980, abandoned, which is a continuation-in-part of Ser. No. 109,420, Jan. 3, 1980, Pat. No. 4,322,449, which is a continuation-in-part of Ser. No. 94,238, Nov. 14, 1979, abandoned.

[51] Int. Cl.[4] .......................... A61K 9/00; A23L 1/00
[52] U.S. Cl. .................................. 426/383; 426/302; 427/3; 424/6; 400/126; 101/35; 118/25
[58] Field of Search ................. 400/126; 426/383, 87, 426/234, 235, 302, 308, 309; 346/140 PD, 75; 424/6, 7, 14; 427/3; 118/24, 25; 101/35

[56] References Cited

U.S. PATENT DOCUMENTS

| | | | |
|---|---|---|---|
| 3,103,165 | 9/1963 | Tripp | 101/35 |
| 3,272,118 | 9/1966 | Ackley | 101/37 |
| 3,831,727 | 8/1974 | Kruspe et al. | 400/126 |
| 3,831,728 | 8/1974 | Woods et al. | 400/126 |
| 3,869,986 | 3/1975 | Hubbard | 101/91 |
| 3,884,143 | 5/1975 | Ackley | 101/37 |
| 3,889,591 | 6/1975 | Noguchi | 101/37 |
| 3,910,183 | 10/1975 | Noren | 101/41 |
| 3,929,071 | 12/1975 | Cialone et al. | 400/126 |
| 4,029,006 | 6/1977 | Mercer | 346/75 |
| 4,069,753 | 1/1978 | Ackley et al. | 101/40 |
| 4,074,279 | 2/1978 | Ikeda et al. | 346/75 |
| 4,104,966 | 8/1978 | Ackley et al. | 101/426 |
| 4,126,503 | 11/1978 | Gardner | 427/2 |
| 4,139,589 | 2/1979 | Beringer | 426/5 |
| 4,158,847 | 6/1979 | Heinzl et al. | 400/126 |
| 4,168,321 | 9/1979 | Okamoto | 426/87 |
| 4,168,662 | 9/1979 | Fell | 426/383 |

OTHER PUBLICATIONS

Graphic Arts Monthly, 6/78, Hartsuch.
IEEE Transactions, 4/72, Kamphoefner.
British Printer, 6/80.

*Primary Examiner*—Steven Weinstein
*Attorney, Agent, or Firm*—Hammond & Littell, Weissenberger & Dippert

[57] ABSTRACT

This invention is directed to a method for the non-contact application of letters or symbols to the exterior surfaces of uncoated tablets or uncoated tablet cores, which comprises dotting color solution or suspension by means of an ink-jet printer in specific quantity in the form of discrete droplets of specific volume onto the exterior surfaces of the uncoated tablets or uncoated tablet cores.

15 Claims, 5 Drawing Figures

METHOD FOR INK-JET PRINTING ON UNCOATED TABLETS OR UNCOATED TABLET CORES

CROSS-REFERENCE TO RELATED APPLICATIONS

This application is a continuation of copending U.S. patent application Ser. No. 284,985, filed July 20, 1981, now abandoned, which in turn is a continuation-in-part of U.S. patent application Ser. No. 147,841, filed May 8, 1980, now abandoned, which in turn is a continuation-in-part of copending U.S. patent application Ser. No. 109,420, filed Jan. 3, 1980, now U.S. Pat. No. 4,322,449, which in turn is a continuation-in-part of U.S. patent application Ser. No. 094,238, filed Nov. 14, 1979, now abandoned.

FIELD OF THE INVENTION

This invention relates to the non-contact printing on pharmaceutical tablets, tablet cores, and tablet-like food comprimates.

BACKGROUND OF THE INVENTION

There are instances when it is appropriate to apply certain markings with regard to pharmaceutical moldings or similar moldings of foods, such as dextrosis or artifical sweeteners in tablet form. Examples of such markings include a bisecting strip, a warning note, an identification code, and a symbol related to intended use, such as a bed for sleeping tablets or a fruit for vitamin tablets. However, the application of desired markings is difficult due to the small size of moldings to be marked as well as the often non-planar surface of such moldings, a problem which also frequently causes difficulties when normal printing procedures, such as, for example, the roller rotation method, are employed.

Methods of contact printing of pharmaceutical moldings are described in several United States patents (see, U.S. Pat. Nos. 4,069,753, 3,272,118, 3,103,165, 3,889,591, 3,910,183, and 4,104,966). Common to all these methods are the problems arising from the facts that the prints smear off easily and that the printing cannot be effected with the same speed at which modern tablet pressing machinery runs. This latter fact means that contact printing is to be done as a special process, no matter what methods are employed.

It has therefore been conventional with regard to tablets to effect lettering or coding by means of engravings in the press tools during the pressing operation itself. It is necessary, in so doing, to provide for each preparation a special pressing tool, for example, a punch, provided with appropriate engravings.

This increases the cost of the manufacture of the moldings to a large extent, especially since, for example, an engraved punch is substantially more expensive than a nonengraved punch. In contrast thereto, an ink-jet-station is so variable that all necessary changes, for example, with regard to the codes, can quickly be arranged. In addition, such an embossing as mentioned above is not easily legible in certain light conditions and, in this respect, makes special demands upon an observer, as well as upon the quality of the granulate used.

Ink-jet systems are well known in the field of paper printing. In U.S. Pat. No. 4,029,006, a method of non-contact printing of cables is described, and in U.S. Pat. No. 4,168,662 an ink for the non-contact printing of food products, e.g., of waxed fruits, eggs, hard candy, and the like, is described, the ink in each case being quick-drying and smear-resistant. In all these cases the surfaces of the printed materials show either an equal hydrophilic or an equal hydrophobic character. The inks used for the printing of such materials can be easily adjusted to the qualities of the surfaces of these materials.

In contrast thereto uncoated tablets or uncoated tablet cores that is, compressed, solid, granulated masses of material, and even every single tablet or core, show varying characteristics with regard to their surfaces as a whole as well as to different zones, or areas, of their surfaces. Dependent upon the qualities of the active ingredients and the additional materials used to build up the granulate to be pressed, the surface of each uncoated tablet or uncoated core shows zones being more hydrophobic and other zones being more hydrophilic. In addition, dependent upon the thickness of the granulates to be pressed, the surface of the uncoated tablet or uncoated core can be either more or less smooth and plain or rough. This means that such a surface shows zones of different absorption which will influence the means in which the ink fluid is dispersed on the surface. Aside from these factors tablets of the same kind show zones of different smoothness and different absorption in the same species due to local differences in pressure exerted on the granulates by the tablet pressing tools.

Tablets usually show a decreased porosity in their fringe zones. The pharmaceutical tablets are, however, to be printed legibly even when they show a diameter of only a few millimeters. With all these facts in mind, as mentioned before, the realization of non-contact printing of tablets and cores with imprints of high quality standards using the ink-jet technique seemed to be out of reach.

DESCRIPTION OF THE INVENTION

It has now been found that moldings of the widest diversity of size, type, and nature of the surface can be lettered or printed easily when the lettering or printing is effected in a non-contact manner with the use of a so-called "ink-jet printer" filled with a foodstuff color solution or suspension. To accomplish this, a color solution or suspension is dotted, i.e., dispersed or sprayed, onto a molding in the form of discrete droplets of equal volume so that as a result of controlled guidance and deflection of the droplets, letter symbols or other symbols such as illustrations or markings, for example, codes, can be placed upon a part of the surface of a molding. A symbol applied in this way is more easily visible, and with pharmaceutical forms of application, such visibility helps to safeguard a patient against confusion when taking medicine. Pharmaceuticals identified in this way not only represent a contribution to achieving a maximum degree of pharmaceutical safety, but they also improve a patient's medicine-taking habits. If pharmaceutical forms such as tablets or coated tables are lettered, for example, before sealing on a blister machine, with the date and time to be taken, then a regular ingestion pattern necessary for a cure may be expected.

An ink-jet printer used within the scope of the invention encompasses a printing device developed per se for high-speed printing on paper by means of computer-controlled writing stations, i.e., terminals. A distinction is made between high-pressure, low pressure, and vacuum pressure processes, depending on the pressure with which a color solution or suspension to be sprayed is supplied to the nozzles of the device.

Figure 3:
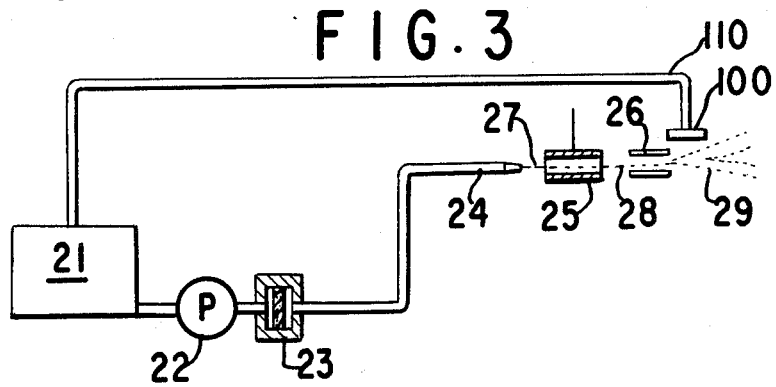
FIG. 3 represents a cross-section of another embodiment of a printing system according to the invention.

In a high-pressure process color solution or suspension emerges as a jet from one or more narrow nozzles. The liquid is supplied to the nozzle under pressure by means of, for example, a pump. Immediately after leaving the nozzle the color solution or suspension disintegrates into individual droplets of equal volume which are deflectable electrostatically or magnetically. Regular contractions in the liquid jet are obtained, due to ultrasonic stimulation. As shown in FIG. 3, fine, uniformly large droplets charged by a charging electrode are deflected electrostatically or electromagnetically to the desired points of the moldings.

Since it is not possible to produce individual droplets, unused droplets are drawn off by means of a "catcher" and the liquid or suspension is guided back into the supply container. Despite this disadvantage, excellent print or letter images are produced with the above-described system, since the generated droplets preferably have a small diameter of about 20 μm.

The number of droplets may amount to approximately 40 in the vertical direction and 20 in the horizontal direction. Due to the smallness of the droplets an uneven dispersion of the ink on the surface of the tablet is avoided, and due to the great quantity of the droplet per symbol a good image or representation of the symbol or letter is produced.

Another advantageous embodiment for the lettering or printing of moldings utilizes the so-called vacuum process (see, U.S. Pat. No. 1,158,847). The system consists, for example, of one or an entire series, 12 or 24, of channels so that a tubular piezoelectric oscillator concentrically surrounds a section of each channel. Conductive layers, for example, silver layers or gold or nickel layers, on the faces of the tubular piezoceramic oscillator, serve as electrodes to apply the electrical field. The individual channels are connected on their feed side, for example, to a common distributor plate connected to a supply container, and are supplied therefrom with the color solution or suspension. (See, FIG. 1).

Backflow of the solution or suspension in the nozzle channel is obstructed due to, for example, the nozzle channel being narrowed towards the outlet opening. As a result of the characteristic of piezoelectric oscillators, for example, piezoceramic masses, to undergo elastic deformation upon the application of a specific electrical field, a shock wave directed to the liquid arises in the tubular piezoelectric oscillators. The pressure increase connected therewith leads to the ejection of very small quantities of color in lobe, or nodule, form from the outlet openings, these lobes, or nodules, of liquid assuming spherical form after leaving the outlet openings. The diameter of a channel is advantageously about 1 mm in its middle part, and the individual channel is narrowed at its outlet opening. The diameter of the outlet opening is, for example, about 0.1 mm.

The supply container lies lower than the outlet openings, which gives rise to a vacuum system. Due to the height difference a static vacuum arises in the channels. This static vacuum is overcompensated for a brief moment in the channels upon the application of the electrical field in conjunction with the capillary action. The capillary forces in the channels and in the outlet openings prevent the color solution or suspension from running back.

One exemplary embodiment of this printing system contains twelve nozzle openings, namely, six each in two off-set rows. The spacing of the nozzle plate from the moldings may be up to 20 mm, preferably from about 1 to 3 mm. The diameter of the droplets is, for example, about 0.1 mm.

The channel which is surrounded by the piezoceramic oscillator may be curved arbitrarily in front of or behind said oscillator. This form of arrangement, i.e., realization, serves for better adaptation to the spatial conditions, e.g., of the tablet press. However, the channel may also be branched into two or more channels spatially after the piezoceramic oscillator, so that one piezoelectric oscillator supplies, i.e., acts upon, several channels with separate outlet openings. The outlet openings may be, e.g., holes in a glass of metal plate. If the channel consists of a glass capillary tube, then the outlet opening may be formed by drawing out the glass tube at its end.

Another advantageous form of arrangement for the lettering or printing of moldings consists of the use of plate-shaped or planar transducers which work on the piezoelectric principle and which are fitted, preferably concentrically, above the entrance of the channels. In this arrangement, narrowed outlet openings are situated at the end of the channels. In a preferred form of arrangement, the piezoelectric plate lies in a distributor compartment horizontally concentrically to the channel leading away vertically. The piezoelectric plates lie in or on a compartment for receiving the color solution or suspension. Several channels may be connected to, i.e., lead away from, a common compartment which is connected, in turn, to a common liquid supply. Thus, for example, a planar oscillator (piezoelectric plate) can also simultaneously generate a pressure wave in several channels connected to the same distributor compartment.

A further advantageous, constructively simplified arrangement comprises a planar oscillator of strong stroke in the distributor compartment and a channel which departs from the distributor compartment and runs preferably vertically to the planar oscillator, the channel having situated at its end several nozzles optionally aligned variously in space or an entire nozzle rim. Due to such an arrangement a surface dotting of the moldings can be obtained with a single stroke generated by the piezoelectric oscillator. (See, FIGS. 2a, 2b, and 2c).

The piezoceramic bodies may also be used as valves if color solution or suspension is supplied under pressure to the oscillator or transducer which opens or closes according to selection. Upon selection, an opening, e.g., a slit-shaped opening, opens briefly in a channel containing the liquid under pressure and the ink is delivered through said opening in drop form.

The printing system preferably used works with tubular or plate-shaped piezoelectric oscillators. Upon the application of a voltage pulse of, for example, 100 volts and a pulse length of 20 microseconds, droplets are ejected at a speed of about 4 m/sec and with a very constant droplet weight of, for example, 0.8 μg (0.0008 mg). Depending on the electronic control, the drop frequency may lie between about 1 and 50,000 drops per second, preferably about 3,000 drops per second.

The symbol or the lettering to be applied is first set in the writing station of the printing system. The printing electronics for the control of the individual nozzles are situated generally on a circuit board which may contain, in addition to power amplifiers for the piezoelectric transducers, a circuit for monitoring the printing liquid.

During the actual printing either the printing head is guided over the moldings or the moldings were guided past the fixed printing head. The printing system works so precisely and quickly that, for example, moldings can be printed at several meters per second, preferably at about 1 m/sec.

Thus, moldings, i.e., tablets or tablet cores, are separated, or delivered, in a row to a conveyor belt which moves past under the nozzle openings of the printing mechanism. During this procedure, the moldings are scanned by, for example, a photocell, so that the printing can be started exactly at the right moment to apply printing precisely at the point of the moldings provided. In this way, it is even possible to print extremely concave or convex moldings.

The non-contact printing operation is best effected in the manufacture of tablets or tablet cores for coating if the molding just pressed in the tableting machine is pushed up out of the cavity by the bottom force, immediately before it is picked up by the so-called scraper. The actual printing operation, namely, the ejection of the color droplets from the individual nozzles at the correct moment, is controlled by the writing station or terminal. For this purpose, the running speed of the tablet press must constantly be transmitted exactly to the electronic mechanism of the writing station by, for example, means of a photocell or a magnetic proximity switch. This is effected by devices known per se to those in the art. The tablet cores are subsequently coated by a transparent film.

Figure 2A:
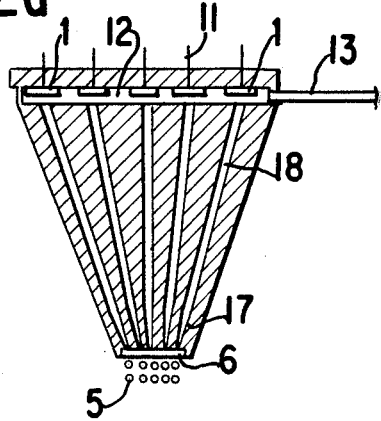
FIGS. 2a, 2b, and 2c represent cross-sections of different dispersing heads with planar transducers.
Figure 2B:
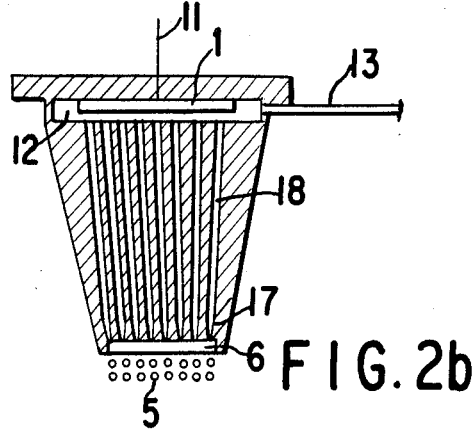
Figure 2C:
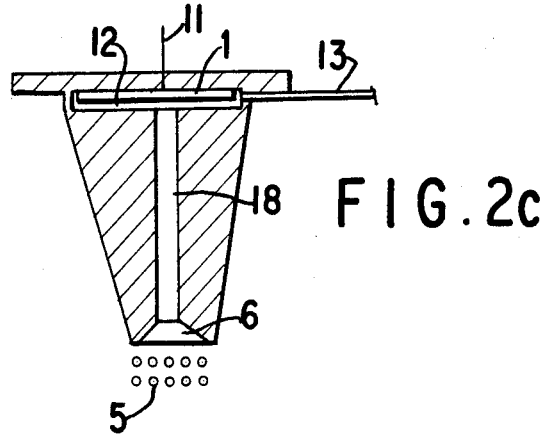

If work is carried out according to FIG. 2c with a printing head which consists of a planar oscillator of strong stroke and a liquid channel at the end of which is situated a nozzle tamplate, then the electronics for the printing operation can be substantially simplified. If, for example, the tablet is detected by a photocell, the printing-on of a symbol or the lettering with a code is effected due to a single stroke of the planar oscillator. This operation may be concluded much more rapidly than in one millisecond, since the printing device adapts itself easily to any tableting speed. Furthermore, the favorable overall height of the printing head is to be emphasized. It may be less than 2 cm high and can thus be accommodated without difficulty on any known tableting machine.

Of course, the system of planar oscillators with nozzle template according to FIG. 2c is also applicable at any other point, such as, for example, on a separating apparatus for tablets or tablet cores or in a coated-tablet printing machine instead of the contact printing device as was conventional hitherto.

Altogether, the complete independence of the printing or lettering from the geometric form of the surface of the moldings is to be emphasized in the process according to the invention. It is unimportant whether the surface is corrugated or if the molding has extremely concave or convex forms. According to the state of the art, in the printing of tablets onlay a small sector of the surface can be printed with contact due to the convex form. With the process according to the invention, the entire curved surface of a tablet can be printed independently of the radius of curvature. Since the operation proceeds in a non-contact manner, smearing, as occurs frequently in the conventional processes, is not possible. Concave tablets cannot be printed by the usual methods.

The color solutions or suspensions employed by means of the above-described devices are appropriately prepared by use of a wetting hydroscopic solvent or suspension agent such as, for example, a lower alkanol, such a methanol, isopropanol, butanol, isobutanol, or ethanol, a mixture of lower alkanols with water, and/or a polyol, such as glycol, polyethyleneglycol, or glycerol. For a better fixing on the surfaces, an adhesive such as methyl cellulose, hydroxypropyl methylcellulose, or hydroxypropyl methylcellulose phthalate may be employed.

Finally, the above-described system of the non-contact printing or lettering of moldings can be used for the inhouse checking of incorrect mixtures and intermixes. If, for example, an active substance is pressed into tablets in two different doses, the tablet with the smaller dose could be provided on the tablet press with one color spot and that with a higher dose could be provided with two color spots. These may be visible colored spots or invisible coding spots fluorescent in, for example, ultraviolet light. Finally, if all tablets are provided with a coding by means of the process according to the invention and if detectors responding to the coding are fitted to the packing machines, then a 100% control of incorrect mix, if any, is possible.

The process according to the invention works substantially more quickly and more precisely than conventional printing methods: 100 or more moldings per second can be printed. The process also works more carefully and is universally applicable, i.e., to solid pharmaceutical tablets and tablet cores. The safety of application of such pharmaceutical forms is increased if, for example, with regard to different doses of the same active substance, clearly visible special codings are printed on moldings to minimize confusion or if the pharmaceutical form is lettered with the specification of the quantity of active substance. With colored coated tablets, the quantity of color can be drastically reduced by coding the cores only with one colored symbol and covering the color-coded cores with a colorless transparent lacquer.

By way of summary, it should be noted that the dotting of moldings may be controlled by, or responsive to, one or more of the following parameters:

(a) the diameter of the outlet opening of the nozzle channels;
(b) the voltage applied to the piezoelectric oscillator;
(c) the droplet frequency;
(d) the number of nozzle channels;
(e) the stroke intensity of the tubular or planar oscillator used;
(f) the concentration of color pigment in the solution or suspension; and
(g) the number of dots needed to imprint the desired symbol.

Figure 1:
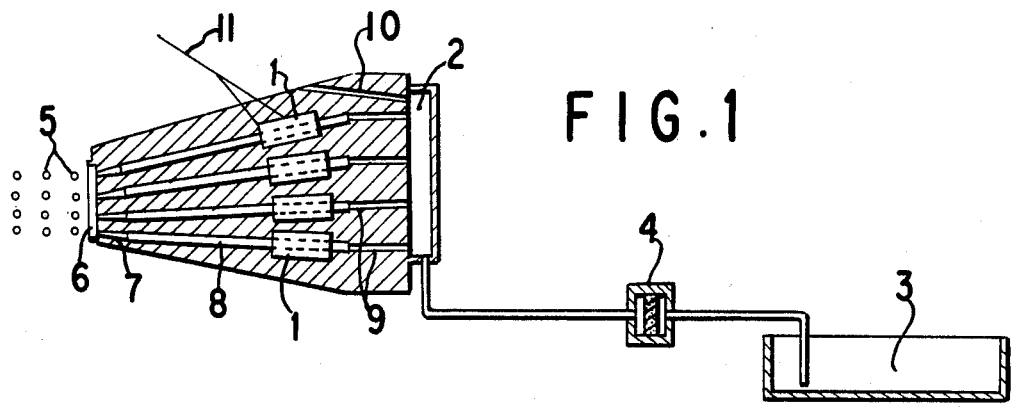
FIG. 1 represents a cross-section of one embodiment of a printing system of this invention.

FIGS. 1 to 3 represent aspects of advantageous systems for non-contact printing of moldings. FIG. 1 shows schematically in cross-section a dotting system with piezoelectric transducers (1) which each surround a nozzle channel (8). The nozzle channel (8) terminates in a narrowing (7), and the individual narrowings (7) occurring at corresponding openings of an outlet nozzle plate (6), whereby the nozzles formed by the narrowings (7) and the openings of the outlet plate (6) deliver droplets of liquid (5) when the device is actuated. The nozzle channel (8) is connected to a liquid distributor compartment (2) via a narrowed liquid channel (9). The distributor compartment (2) has a venting channel (10), and the distributor compartment (2) is connected via a filter plate (4) to a liquid supply container (3). The electrical control of the piezoelectric transducers is effected via contacts (11).

FIGS. 2a, 2b, and 2c represent cross-sections of variously constructed dotting heads with planar transducers working on the piezoelectric principle. Here, planar piezoelectric transducers (1) have contacts (11) for electrical control. The planar piezoelectric transducers lie in a liquid distributor compartment (12) which is connected via the liquid line (13) to a supply container. One or more nozzle channels (18), whose narrowings (17) terminate at an outlet nozzle plate (6), lead away from the distributor compartment (12). Liquid droplets (5) are released from the nozzle plate (6).

FIG. 3 is a schematic cross-section of a so-called high-pressure dotting system. From a liquid supply container (21) ink is pressed by means of a pump (22) through a filter (23) into a nozzle (24). An ink jet (27) released at the nozzle (24) is decomposed, i.e., broken, into drops (28) which are charged electrically by a drop charging ring (25) and are deflected by means of a deflector plate (26) in an electrical field. The deflected liquid drops (29) letter the moldings. The remaining, i.e., undeflected, drops (29) are drawn up by a "catcher" (100) and collected and are returned to the container (21) via line (110).

The following examples are intended to illustrate the invention and are not to be construed as limiting the invention thereto.

EXAMPLE 1

Ten thousand multi-vitamin tablets were laid in a row on a high-speed conveyor belt provided with a corresponding groove. The symbol of an orange was sprayed onto them by means of a printing system which worked according to the vacuum process and a piezoelectrically generated shock wave, which system contained an edible orange solution in isopropanol (with a small addition of glycerol). The passing coated tablets were scanned by means of a photocell, and the timing of the spraying operation was adjusted correspondingly.

EXAMPLE 2

At a tableting speed of 100,000 tablets per hour, 8 mm moldings were printed with a code immediately before the scraper with a printing device consisting of a planar oscillator and a nozzle template. The printing operation was started by means of a photocell. The printing suspension consisted of a micronised iron oxide in glycol. The code applied, 38C/38C, consisted of 150 droplets with a droplet weight of about 0.0006 mg. The quantity of color per tablet was about $9\gamma = 0.009$ mg. The excitation of the planar oscillator was concluded after 0.3 milliseconds. The diameter of the droplet was about 100 $\mu$m.

EXAMPLE 3

In a separating apparatus, 9 mm tablets were placed upright and printed on the front and rear sides. The two printing heads worked according to the vacuum system, each consisting of 12 nozzles. The preparation name (10 letters) was printed on the front side and the dose (50 mg) was printed on the rear side. The color solution was a saturated aqueous orange solution.

The feed speed was 1 m/sec, and 150,000 tablets per hour were printed. The droplet frequency of the vacuum system was 3,000 droplets per second.

EXAMPLE 4

In accordance with Example 3 tablet cores were singled out upon leaving the tablet pressing machinery by means of a separating apparatus and were printed by means of printing heads, which worked according to the vacuum system and which each consisted of 24 nozzles. The average distance between the nozzle endings and the tablet cores are about 3 mm. On the front and rear sides of the cores symbols were imprinted. An alkanolic aqueous erythrosin solution was used as an ink, which solution was adjusted to the necessary surface tension, density, and viscosity by the addition of hydroxypropyl methylcellulose. After the printing operation the tablet cores were coated in the usual way by a transparent lacquer, which made the symbols easily visible.

The preceding specific embodiments are illustrative of the practice of the invention. It is to be understood, however, that other expedients known to those skilled on the art or disclosed herein, may be employed without departing from the spirit of the invention or the scope of the appended claims.

We claim:

1. In a method for applying indicia to the exterior surfaces of uncoated tablets or uncoated tablet cores comprising compressed, solid, granulated masses of material, where said exterior surfaces are non-uniform with regard to one or more properties of surface tension, texture, and absorbency, the improvement which comprises dotting onto said exterior surfaces of said uncoated tablets or uncoated tablet cores color solution or suspension by means of an ink-jet printer in specific quantity in the form of discrete droplets of specific volume to form indicia on said exterior surfaces of said uncoated tablets or uncoated tablet cores, said dotting being effected so that said indicia are applied to said exterior surfaces at a high speed.

2. The method of claim 1, wherein the ink-jet printer works according to the vacuum process and employs a shockwave generated by a piezoelectric dotting system.

3. The method of claim 1, wherein the ink-jet printer works according to a low pressure process.

4. The method of claim 1, wherein the ink-jet printer works according to a high-pressure process.

5. The method of claim 1, wherein each ink-jet printer applies indicia to 100 or more uncoated tablets or uncoated tablet cores per minute.

6. The method of claim 1, wherein said uncoated tablet or uncoated tablet cores are foodstuffs.

7. The method of claim 6, wherein after the solution or suspension is dotted onto said exterior surfaces, said surfaces are coated with a transparent lacquer.

8. The method of claim 1, wherein the droplets have a diameter of from about 1 to 150 $\mu$m.

9. The method of claim 8, wherein the droplets have a diameter of from about 20 to 100 μm.

10. The method of claim 1, wherein said uncoated tablets or uncoated tablet cores are pharmaceutical tablets or table cores and wherein the ink-jet printer works according to the vacuum process and employs a shock-wave generated by a piezoelectric dotting system.

11. The method of claim 10, wherein after the solution or suspension is dotted onto said exterior surfaces, said surfaces are coated with a transparent lacquer.

12. The method of claim 10, wherein each ink-jet printer applies indicia to 100 or more uncoated tablets or uncoated tablet cores per minute.

13. The method of claim 1 or 10, wherein said indicia are applied to said exterior surfaces as said uncoated tablets or uncoated tablet cores are pushed up from the molds of a tablet press.

14. The method of claim 1 or 10, wherein said indicia are applied to said uncoated tablets or uncoated tablet cores aligned in a row on a conveyor belt.

15. The method of claim 1 or 10, wherein said uncoated tablet or uncoated tablet cores are printed with solutions or suspensions of food colors in lower alkanols, lower alkanol-water mixtures, polyols, or a combination of two or more thereof.

* * * * *

UNITED STATES PATENT AND TRADEMARK OFFICE
CERTIFICATE OF CORRECTION

PATENT NO. : 4,548,825
DATED : October 22, 1985
INVENTOR(S) : GÜNTHER VOSS et al.

It is certified that error appears in the above-identified patent and that said Letters Patent is hereby corrected as shown below:

Column 2, line 10, "cores" should read -- cores, --.

Column 5, line 46, "tamplate" should read -- template --.

Column 6, line 2, "onlay" should read -- only --.

Claim 6, line 2, "tablet or" should read -- tablets or --.

Claim 15, line 2, "tablet or" should read -- tablets or --.

Signed and Sealed this

Eleventh Day of February 1986

[SEAL]

Attest:

DONALD J. QUIGG

Attesting Officer

Commissioner of Patents and Trademarks